(12) United States Patent
Pletnev

(10) Patent No.: US 9,226,872 B2
(45) Date of Patent: Jan. 5, 2016

(54) APPARATUS FOR TREATING AND/OR PREVENTING DISEASES AND FUNCTIONAL DISORDERS OF EXTERNAL GENITAL ORGANS

(76) Inventor: Sergey Vladimirovich Pletnev, Minsk (BY)

( * ) Notice: Subject to any disclaimer, the term of this patent is extended or adjusted under 35 U.S.C. 154(b) by 0 days.

(21) Appl. No.: 13/501,696

(22) PCT Filed: Dec. 29, 2009

(86) PCT No.: PCT/IB2009/055987
§ 371 (c)(1),
(2), (4) Date: Apr. 12, 2012

(87) PCT Pub. No.: WO2011/045632
PCT Pub. Date: Apr. 21, 2011

(65) Prior Publication Data
US 2012/0203055 A1    Aug. 9, 2012

(30) Foreign Application Priority Data
Oct. 12, 2009   (EA) .................................. 200901468

(51) Int. Cl.
*A61N 1/00*   (2006.01)
*A61H 19/00*   (2006.01)
(Continued)

(52) U.S. Cl.
CPC .............. *A61H 19/32* (2013.01); *A61N 2/002* (2013.01); *A61H 2201/10* (2013.01);
(Continued)

(58) Field of Classification Search
CPC .............. A61N 2/02; A61N 2/06; A61N 2/12; A61N 2/002; A61N 2/004; A61N 5/0616
USPC ............................................ 600/9, 13, 14, 37
See application file for complete search history.

(56) References Cited

U.S. PATENT DOCUMENTS 6,249,698 B1 *   6/2001   Parris ................................. 607/3
2007/0027411 A1 *   2/2007   Ella et al. .......................... 601/7
(Continued)

FOREIGN PATENT DOCUMENTS

| CA | 2282723 A1 | 3/2001 |
|---|---|---|
| RU | 2153366 C1 | 4/2000 |
| WO | WO98/25667 A1 | 6/1998 |
| WO | WO 0040294 A1 * | 7/2000 |

OTHER PUBLICATIONS

Int. Search Report for PCT/IB2009/055987, Jun. 17, 2010.

*Primary Examiner* — John Lacyk
(74) *Attorney, Agent, or Firm* — Sean Wooden; Andrews Kurth LLP

(57) ABSTRACT

The present invention relates to a method for treatment and/or prevention of diseases and functional disorders of external genital organs and a device for realizing the same. The method comprises exposure of an organ to periodic action of vacuum oscillations and a light field and is characterized in that the organ is additionally exposed to low-frequency pulsed magnetic field and the light exposure of different wavelengths is combined. One of the embodiment of the device comprises a source of vacuum with a periodic controlling device, an isolated chamber adapted to accommodate a to-be-exposed organ therein, a source of a low-frequency pulsed magnetic field with an inductor generating a magnetic field in the place of location of the organ to be subjected to exposure. The claimed embodiment is characterized in that it additionally comprises a light exposure source with different wavelengths and a device for synchronizing and combining the light exposure.

5 Claims, 1 Drawing Sheet

Figure 1:
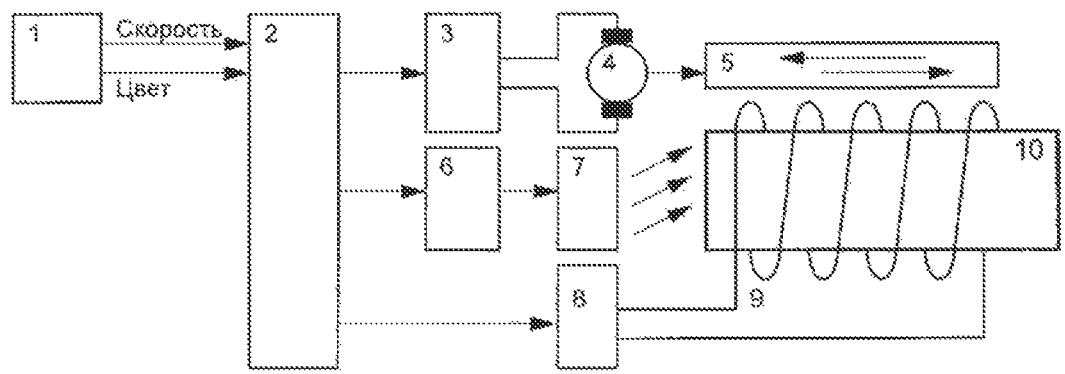

(51) Int. Cl.
  *A61N 2/00* (2006.01)
  *A61N 5/06* (2006.01)
(52) U.S. Cl.
  CPC ............... *A61H 2201/5035* (2013.01); *A61H 2201/5038* (2013.01); *A61N 5/0616* (2013.01); *A61N 2005/0643* (2013.01); *A61N 2005/0652* (2013.01); *A61N 2005/0663* (2013.01)

(56) References Cited

U.S. PATENT DOCUMENTS

2008/0243197 A1  10/2008  Bove
2009/0005631 A1*  1/2009  Simenhaus et al. ............... 600/9

* cited by examiner

Rate

Color

Color

APPARATUS FOR TREATING AND/OR PREVENTING DISEASES AND FUNCTIONAL DISORDERS OF EXTERNAL GENITAL ORGANS

The present invention is related to the field of medical equipment, specifically to means for treating and preventing diseases and functional disorders (stimulating) genital organs.

A number of methods and apparatuses have been proposed for treatment of impotence by exposing an organ to mechanical oscillations and a magnetic field (International Application WO2005041845).

The method and apparatus have been proposed for a combined action of vacuum and infrared light (AMVL-01 apparatus developed by "Yarovit-Yar Ltd".).

The above methods are efficient for treatment and prevention of functional disorders and a number of diseases.

Such methods and apparatuses, however, are useful for treatment of a limited range of diseases.

A number of methods and apparatuses for treatment of impotence and scleroderma using the periodic exposure to vacuum and a traveling magnetic field has been proposed (RF Pat. No. 2,072,822).

This method is also useful only for treatment of impotence and localized scleroderma.

The objective of the present invention is to expand therapeutic capacities and improve efficiency.

The objective of the present invention is achieved by providing the method for treatment and/or prevention of diseases and functional disorders of external genital organs comprising exposure of an organ to periodic action of vacuum and/or mechanical oscillations and low-frequency pulsed magnetic field and an additional exposure to a light field, with the light exposure of different wavelengths being combined.

It should be noted that the value of the magnetic field exposure is set in the range of 3-50 mT.

The further improvement is characterized by the fact that the pulsed magnetic field is synchronized with periodic mechanical oscillations and/or pressure oscillations.

Then, the pulsed magnetic field is synchronized with the pulsed light exposure.

Embodiments of devices for realizing the method comprise a source of mechanical oscillations and/or a source of vacuum oscillations with a periodic controlling device, an isolated chamber adapted to accommodate a to-be-exposed organ therein, a source of a low-frequency pulsed magnetic field with an inductor generating a magnetic field in the place of location of the organ to be subjected to exposure. The device is characterized in that it additionally comprises a light exposure source with different wavelengths and a device for synchronizing and combining the light exposure.

This combined exposure produces synergistic effect which enhances therapy intensity, substantially expands the rage of curable diseases and also significantly increases prevention efficiency. Additional light exposure makes it possible to treat an expanded range of diseases, for example, skin, blood and other diseases. In addition, such an intensive and combined effect on blood circulating the organ during the procedure is similar to the blood treatment by exfusion. It is noteworthy that a portion of blood which is actually treated over the entire procedure in the effective volume due to erection, is then flows through a body and produces therapeutic effect on other organs, thereby substantially stimulating functioning of all organs and improving the body resistance to other diseases.

Therefore, a combined, multimode effect of the pulsed magnetic field, multifunctional optical radiation due to an extensive use of different wavelengths, light flux polarization and also vacuum pull provide three main principles of physiotherapy: synergism, complementarity and partial antagonism that allows not only the list of diseases to be extended, but also—which is the most important of all that—the treatment quality to be improved and treatment time to be reduced.

A fuller understanding of the present invention will be had from the following description in which the preferred embodiments is set forth in conjunction with accompanying drawings in which:

FIG. 1—an alternative embodiment of a block-diagram of the device with a combined mechanical, magnetic and light exposure.

Figure 2:
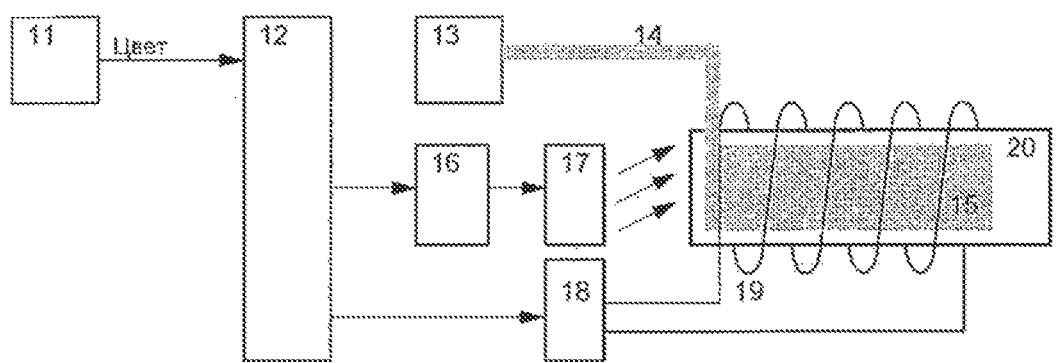

FIG. 2—an alternative embodiment of a block-diagram of the device with a combined vacuum, magnetic and light exposure.

It will be readily understood by those skilled in the art that these devices may be integrated.

Referring to FIG. 1, the device of the present invention comprises a control panel 1 coupled with a microcontroller 2 to enable and disable respective actions and control the rate and frequency of mechanical oscillations and combinations of the light exposure. A control unit 3 of an electric motor 4 which puts a mechanical masseur 5 into operation is connected to a respective output of the microcontroller 2. A control unit 6 of a light-emitting diode array 7 is connected to the second output of the microcontroller 2. A control unit 8 of an electromagnetic inductor 9 is connected to the third output of the microcontroller 2. The electromagnetic inductor 9 encloses an isolated flask 10 made of a light transmissive material. The mechanical masseur 5 is actually disposed on the inner surface of the flask 10 and is provided with flexible gripping means.

The light-emitting diode array 7 is disposed outside in proximity to the light transmissive surface of the flask 10.

The principle of operation of the device is as describe hereinafter. A to-be-treated organ is inserted into the flask 10. Then the flexible gripping means of the mechanical masseur 5 softly encloses it. The control panel 1 is used to set the rate and frequency of mechanical oscillations and also color combinations of the light and sequence thereof. Parameters of mechanical oscillations are adjusted individually. Combinations of color of the light are program-set by guidelines of a physician or based on the sequential combination of the entire color set of the light-emitting diodes in the array. Frequency and intensity of magnetic field pulses may be also varied on physician's order or through the program based on the set standard sequences. The procedure time is also program-set or is stopped in case of onset of orgasm. The mechanical magnetic and phototherapeutic action is synchronized by the microcontroller 2, with the procedure duration being 10 minutes and increasing by 2 minutes each day reaching 20 minutes and then reducing down to 14 minutes. The treatment or prevention cycle reaches 10-12 days.

Referring to FIG. 2, the device of the present invention comprises a control panel 11 coupled with a microcontroller 12 to enable and disable respective actions and combinations of the light exposure. A pneumatic bulb 13 is connected with a hose 14 and a pneumatic sleeve 15. Pressure in the system is controlled and set individually. A control unit 16 of a light-emitting diode array 17 is connected to the output of the microcontroller 2. A control unit 18 of an electromagnetic inductor 19 is connected to the second output of the microcontroller 2. The electromagnetic inductor 19 encloses an isolated flask 20 made of a light transmissive material. The pneumatic sleeve 15 is disposed on the inner surface of the flask 20 and is provided with elastic sealing.

The light-emitting diode array 17 is disposed outside in proximity to the light transmissive surface of the flask 20.

The principle of operation of the device is as describe hereinafter. A to-be-treated organ is inserted into the flask 20. Then the elastic sealing of the pneumatic sleeve 15 softly encloses it. The control panel 11 is used to set color combinations and sequence thereof. Pressure parameters are adjusted individually. Combinations of color of the light are program-set by guidelines of a physician or based on the sequential combination of the entire color set of the light-emitting diodes in the array. Frequency and intensity of magnetic field pulses may be also varied on physician's order or through the program based on the set standard sequences. The procedure time is also program-set or is stopped in case of onset of orgasm.

The vacuum exposure is selected by each patient individually with consideration for individual features, then the magnetic and phototherapeutic actions are synchronized, with the procedure duration being 10 minutes and increasing by 2 minutes each day reaching 20 minutes and then reducing down to 14 minutes. The treatment or prevention cycle reaches 10-12 days.

The magnetic field value may be varied within the range of 3-50 mT and is set on the average at 10+/−5 mT. The light flux value is 2+/−1 mW.

The test conducted has demonstrated high efficiency of the claimed methods and devices. The methods and devices may be actually used for treatment of any diseases of organs in combination with the general exposure of organism to the above described factors.

The invention claimed is:

1. A method for treatment and/or prevention of diseases and functional disorders throughout an organism comprising exposing an external genital organ to a periodically applied suction and simultaneously exposing an organ to a pulsed light field of different wavelengths while simultaneously exposing the organ to a low-frequency pulsed magnetic field; and combining the pulsed light field and synchronizing with the pulsed magnetic field and periodic action of suction.

2. The method according to claim 1 wherein the amplitude of the pulsed magnetic field is selected in the range of 3-50 mT.

3. A device for realizing the method according to claim 1 comprising a source of suction with a periodic controlling device, an isolated chamber adapted to accommodate a to-be-exposed organ therein and a light exposure source with different wavelengths, wherein the device additionally comprises a source of a low-frequency pulsed magnetic field with an inductor generating a magnetic field in the place of location of the organ to be subjected to exposure, and a device for synchronizing and combining the light exposure with magnetic pulses.

4. The method according to claim 1, wherein the periodically applied suction is applied for at least approximately 10 minutes.

5. The method according to claim 1, wherein the periodically applied suction is applied for at least long enough to induce erection.

* * * * *